US008070788B2

(12) United States Patent
Kim

(10) Patent No.: US 8,070,788 B2
(45) Date of Patent: Dec. 6, 2011

(54) HOT PAD ASSEMBLY FOR PEDICURE

(76) Inventor: Jonathan Kim, Monsey, NY (US)

( * ) Notice: Subject to any disclaimer, the term of this patent is extended or adjusted under 35 U.S.C. 154(b) by 422 days.

(21) Appl. No.: 12/478,072

(22) Filed: Jun. 4, 2009

(65) Prior Publication Data
US 2010/0312316 A1 Dec. 9, 2010

(51) Int. Cl.
A61F 7/02 (2006.01)
(52) U.S. Cl. .......................... 607/108; 607/112; 607/114
(58) Field of Classification Search .................. 607/108, 607/112, 114
See application file for complete search history.

Primary Examiner — Roy Gibson
Assistant Examiner — Jared W Pike
(74) Attorney, Agent, or Firm — John K. Park; Park Law Firm

(57) ABSTRACT

A hot pad assembly for pedicure comprises a hot pad comprising means for absorbing heat and releasing heat over a period of time, a hot pad attachment means to secure the hot pad around the knee, a hot pad cover shaped to fit and cover the hot pad having a plurality of means for securing the hot pad assembly around the shin and calf, and a leg cover for being placed between the leg and the pad cover having the hot pad therein. A beauty product is applied to the leg and the leg cover encloses the product and the leg together to improve the effectiveness of the beauty care product with the help of heat transfer from the hot pad.

19 Claims, 6 Drawing Sheets

HOT PAD ASSEMBLY FOR PEDICURE

BACKGROUND OF THE INVENTION

The present invention relates to a hot pad assembly 10 for pedicure. More particularly, this invention relates to a hot pad assembly 10 secured to a person's leg for pedicure, which keeps a leg warm during a pedicure, wherein the assembly 10 comprises a hot pad 30, a hot pad attachment means 36, 38, a pad cover 50 and a leg cover 80.

A pedicure is a cosmetic care or treatment of the feet and their nails. The steps for pedicure may involve the treatment of the whole foot wherein the foot is generally treated through the application of creams, lotions, hot wax, skin-conditioning softeners, or other beauty products.

Keeping a leg and foot warm is known to be effective in facilitating comfort and relaxation and keeping blood flowing freely, which are the key to better results for pedicure. Pedicure spas have been used for such treatment and comfort of the feet of a person in the steps for pedicure. However, spar treatment has to be separated from other steps of pedicure and the time lag between the spar treatment and other steps reduces the effectiveness of the spar treatment.

Accordingly, a need for a hot pad assembly secured to a person's leg for pedicure has been present for a long time given the lack of method to keep a leg warm and applying other steps of pedicure at the same time. This invention is directed to solve these problems and satisfy the long-felt need.

SUMMARY OF THE INVENTION

The present invention contrives to solve the disadvantages of the prior art.

An object of the invention is to provide a hot pad assembly 10 for pedicure to provide a means for keeping a leg warm during pedicure.

Another object of the invention is to provide a hot pad assembly 10 secured to a person's leg for pedicure wherein a hot pad keeps a leg warm to improve the effectiveness of a beauty product applied to the leg.

Still another object of the invention is to provide a a hot pad assembly secured to a person's leg for pedicure to help muscle relaxation and comfort and keep smooth blood flow, increasing the effectiveness of pedicure in general.

An aspect of the invention provides a hot pad assembly 10 secured to a person's leg for pedicure, comprising a hot pad comprising means for absorbing heat and releasing heat over a period of time, wherein the part of the hot pad covering a knee is circular and the part of the hot pad covering a shin and a calf comprises cuts to fit the contour of the shin and calf; a hot pad attachment means 36, 38 to secure the hot pad around the knee; a pad cover 50 comprising a first layer and a second layer to cover the hot pad 30, wherein the first layer and the second layer are shaped to fit and cover the hot pad 30, comprising a plurality of means, 52, 54, 56, 58, 60, 62, 64, 66, 72, 74, 76, 78, 80, 82, 84, 86 between cuts on both sides, for securing the hot pad assembly around the shin and calf; and a leg cover 90 for covering the leg and a beauty product applied to the leg.

Another aspect of the invention provides a method for using a hot pad assembly secured to a person's leg for pedicure, comprising steps of applying a beauty product to a leg (S 100); wrapping or covering the leg with a leg cover such as plastic wrap, towel or fabric (S 200); placing a pad cover having a hot pad therein on the leg cover for conveying heat from the hot pad to the leg and beauty product (S 300); and securing the pad cover having the hot pad therein around the leg (S 400).

The advantages of the present invention are: (1) the hot pad assembly can improve the effectiveness of the beauty care product applied to a leg; and (2) the hot pad assembly can help the leg muscle's relaxation and comfort and keep the blood flow smooth.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION EMBODIMENTS OF THE INVENTION

FIGS. 1-3 and 5 show a hot pad assembly 10 according to an embodiment of the present invention. FIG. 4 shows a hot pad assembly 10 according to another embodiment of the invention.

Figure 1:
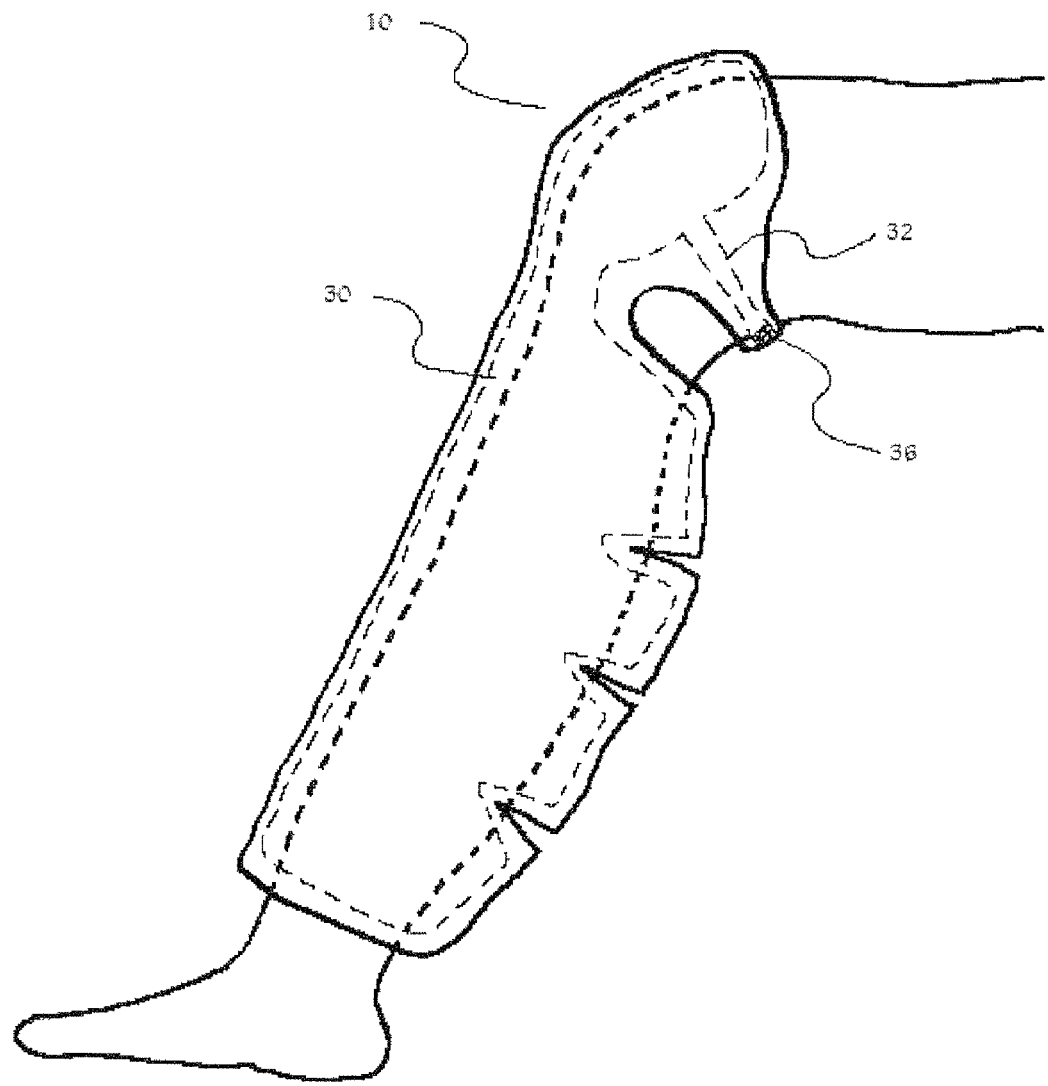
FIG. 1 is a side view showing a hot pad assembly 10 secured to a person's leg for pedicure according to an embodiment of the present invention.

FIG. 1 shows a hot pad 10 assembly secured to a person's leg for pedicure, comprising a hot pad 30 comprising means for absorbing heat and releasing heat over a period of time, wherein the part of the hot pad covering a knee is circular and the part of the hot pad covering a shin and a calf comprises cuts to fit the contour of the shin and calf; a hot pad attachment means 36, 38 to secure the hot pad 30 around the knee; a hot pad cover 50 comprising a first layer and a second layer to cover the hot pad 30, wherein the first layer and the second layer are shaped to fit and cover the hot pad 30, comprising a plurality of means, 52, 54, 56, 58, 60, 62, 64, 66 between cuts on both sides, for securing the hot pad assembly 10 around the shin and calf; and a leg cover 90 for being placed between the leg and the pad cover 50 having the hot pad 30 therein, wherein the leg cover 90 is applied directly to the said leg.

Figure 2:
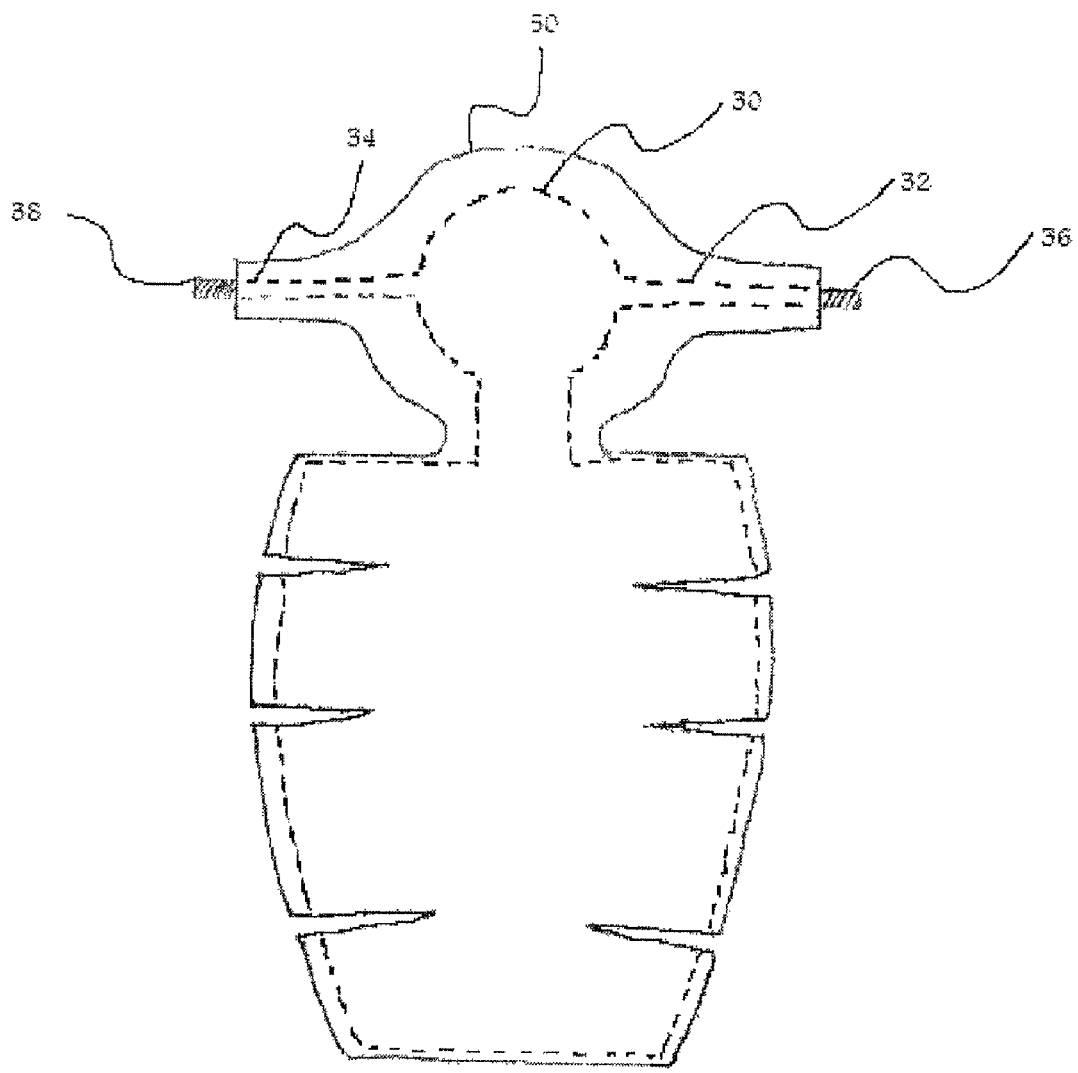
FIG. 2 is a plan view showing a hot pad 30 located in a hot pad cover 50 according to an embodiment of the present invention.

FIG. 2 shows a hot pad 30 according to an embodiment of the present invention. The hot pad 30 may be microwave-heatable, boiling-heatable or heatable by other means. The hot pad 30 may be electric and the temperature of the hot pad may be pre-set. The hot pad 30 may be yellow soil pad or hwangto pad. Yellow soil pad or hwangto pad is known for its medicinal effects such as removing toxins from the body, preventing aging, promoting metabolism, preventing chronic fatigue, preventing various types of adult disease, treating burns and preventing red tide phenomena. Thus, using yellow soil pad or hwangto pad in connection with pedicure can improve the effectiveness of pedicure.

The warming of the hot pad 30 may last for 10-15 minutes. The warming may last longer, but 10-15 minutes of stable heat transfer is appropriate for the application of beauty product to a leg. 10-15 minutes are also appropriate because prolonged use of a hot pad on one area of the body can cause a burn.

The part of the hot pad 30 covering a knee may comprise two strap-shaped parts 32, 34 extended on both sides thereof having means 36, 38 for fastening or attachment. The fastening or attachment means 36, 38 may have fabric hook-and-loop fasteners.

Figure 3:
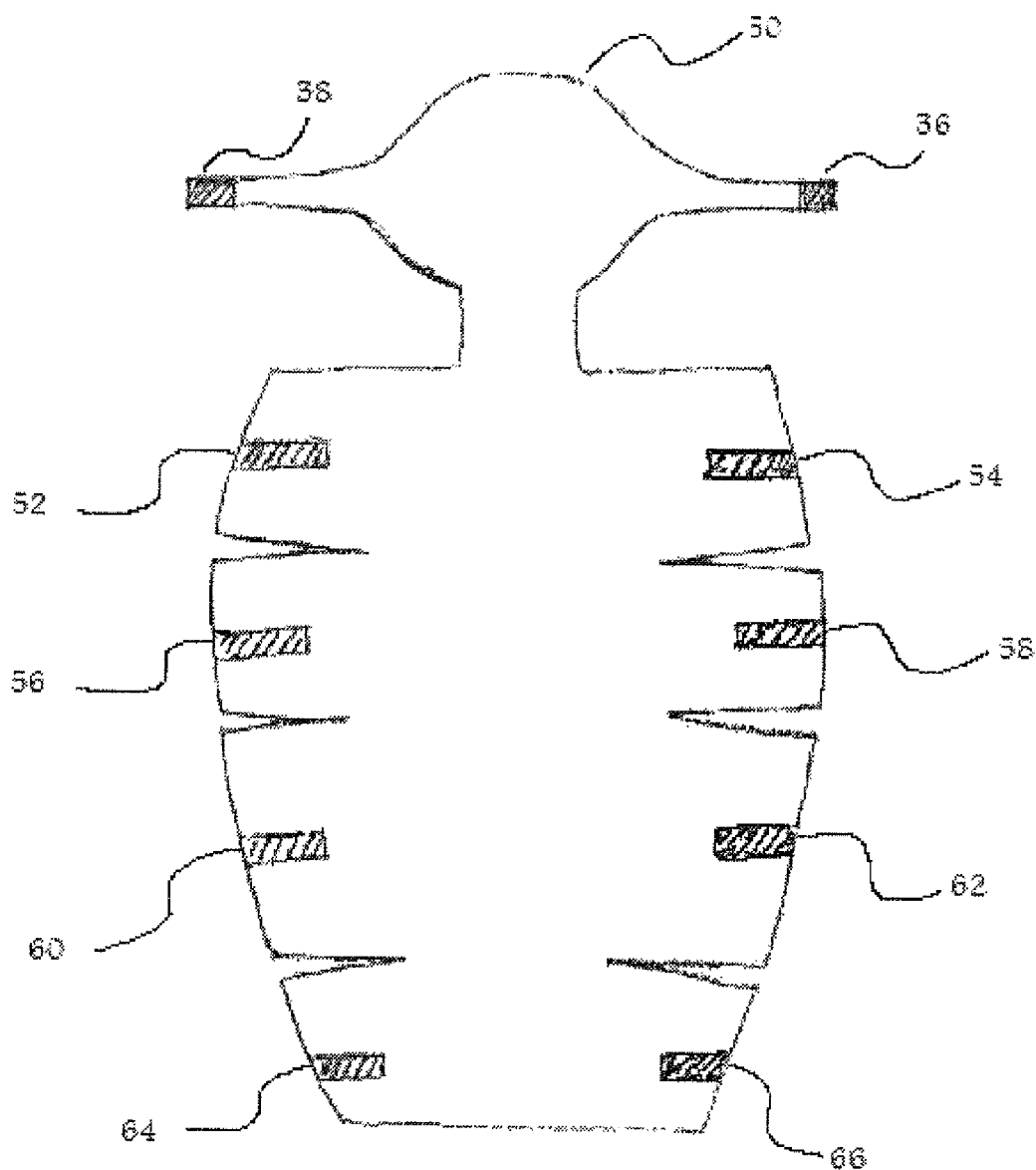
FIG. 3 is a plan view showing a hot pad cover 50 having a plurality of means 52, 54, 56, 58, 60, 62, 64, 66 for attachment.
Figure 4:
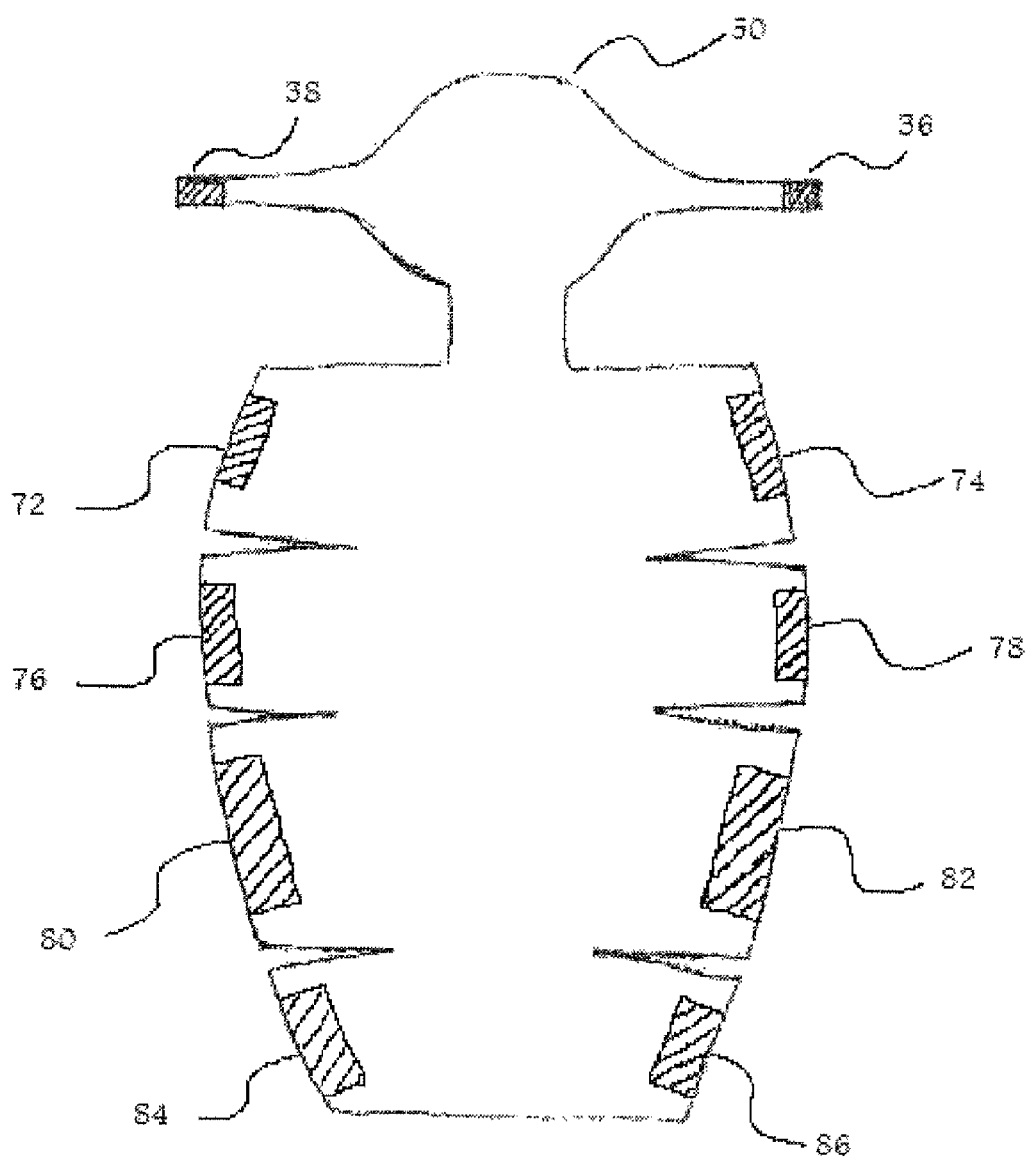
FIG. 4 is a plan view showing a hot pad cover having a plurality of alternative means 72, 74, 76, 78, 80, 82, 84, 86 for attachment.

FIG. 3 shows a hot pad cover 50 according to an embodiment of the present invention. The first layer and the second layer of the pad cover 50 may be similarly shaped. The layers may comprise a pocket for the hot pad 30. In addition, the first layer and the second layer of the pad cover 50 may be made of fabric.

The pad cover 50 comprises means for fastening or attachment 52-66 on both sides for securing the hot pad assembly around the leg. The pad cover may comprise fabric hook-and-loop fasteners on both sides for securing the hot pad assembly around the leg. The layout of attachment means 52-86 may be as in FIG. 3 or FIG. 4.

Figure 5:
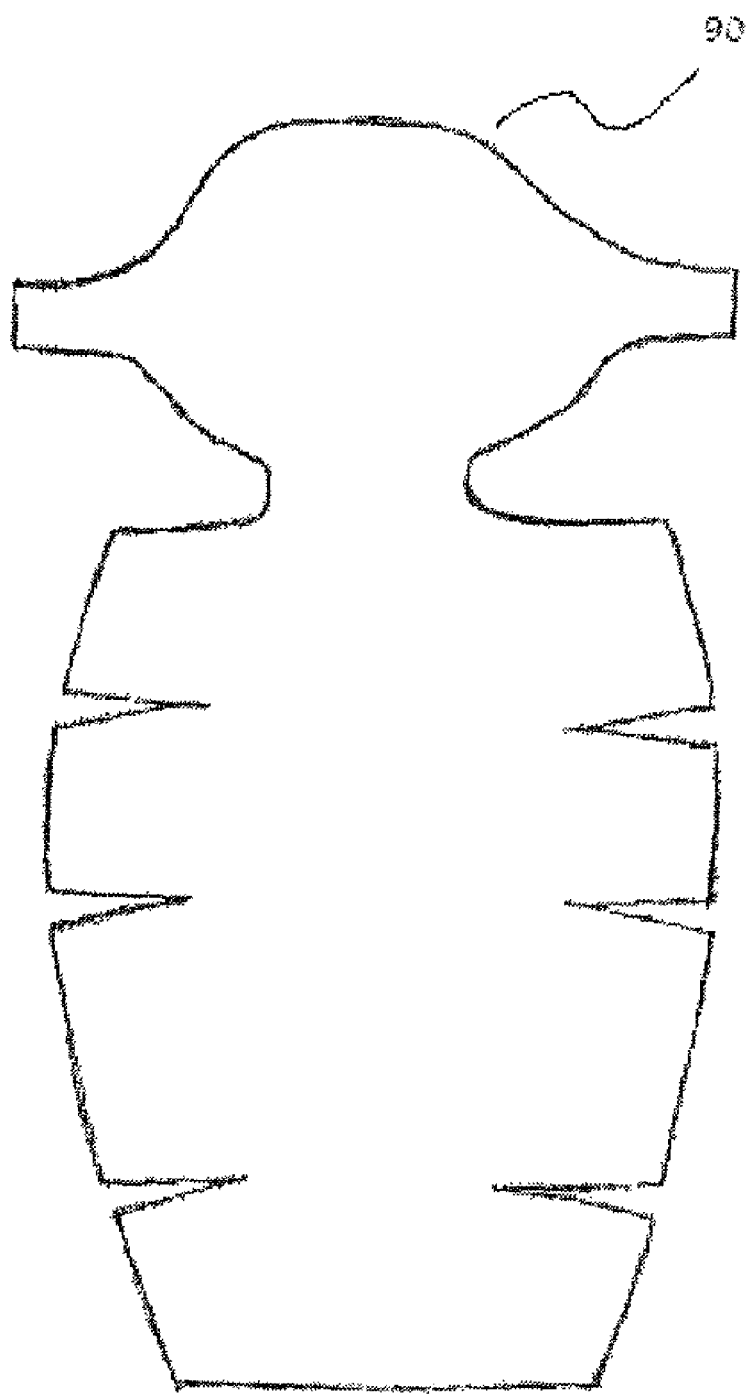
FIG. 5 is a plan view showing a leg cover 90.

FIG. 5 shows a leg cover 90 according to an embodiment of the present invention. The leg cover 90 and pad cover 50 may be similarly shaped. The leg cover 90 may be made of fabric or towel. The leg cover may be made of plastic wrap. Additionally, the leg cover 90 may be disposable.

In the alternative embodiment, the pad cover 50 and the leg cover 90 may be integrated into one inseparable unit.

A beauty product may be applied to the leg and the leg cover 90 encloses the product and the leg together. The material and thickness of the pad cover 50 and the leg cover 90 may be configured to have the temperature of inside leg cover contacting a leg to be 42-46° C. (Celsius).

Figure 6:
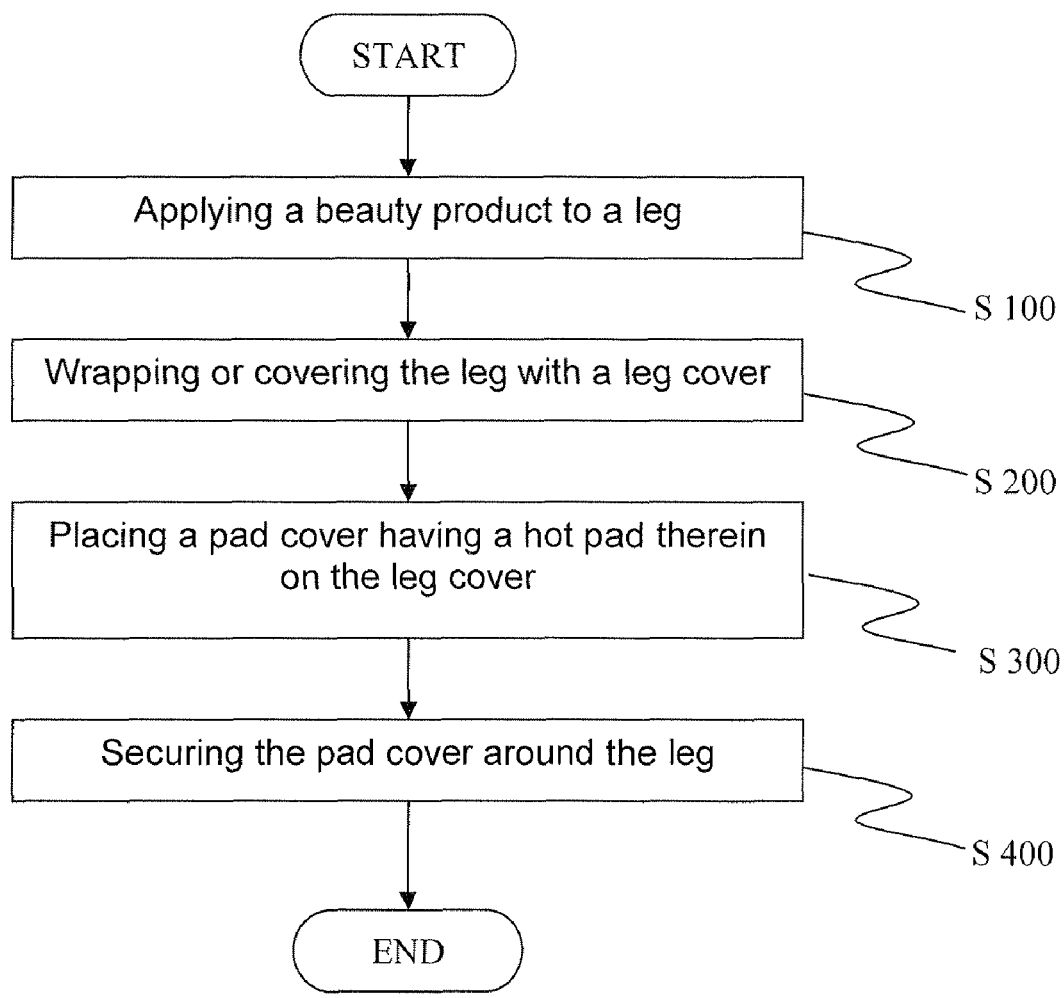
FIG. 6 is a flow chart showing the steps for a method for using a hot pad assembly.

FIG. 6 shows the steps for a method for using a hot pad assembly 10. A method for using a hot pad assembly 10 secured to a person's leg for pedicure comprises steps of applying a beauty product to a leg (S 100); wrapping or covering the leg with a leg cover such as plastic wrap, towel or fabric (S 200); placing a pad cover having a hot pad therein on the leg cover for conveying heat from the hot pad to the leg and beauty product (S 300); and securing the pad cover having the hot pad therein around the leg (S 400).

The steps of FIG. 6 may additionally include a step that two strap-shaped parts 32, 34 extended from the part of the hot pad covering a knee may be fastened or attached around the knee for securing the hot pad around the knee.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. A hot pad assembly secured to a person's leg for pedicure, comprising:
   a hot pad comprising means for absorbing heat and releasing heat over a period of time, wherein the part of the hot pad covering a knee is circular and the part of the hot pad covering a shin and a calf comprises cuts to fit the contour of the shin and calf; wherein the hot pad is yellow soil pad or hwangto pad
   a hot pad attachment means to secure the hot pad around the knee;
   a hot pad cover comprising a first layer and a second layer to cover the hot pad, wherein the first layer and the second layer are shaped to fit and cover the hot pad, comprising a plurality of means between cuts on both sides for securing the hot pad assembly around the shin and calf; and
   a leg cover for being placed between the leg and the pad cover having the hot pad therein, wherein the leg cover is applied directly to the said leg.

2. The hot pad assembly of claim 1, wherein the hot pad is microwave-heatable.

3. The hot pad assembly of claim 1, wherein the warming of the hot pad lasts for 10-15 minutes.

4. The hot pad assembly of claim 1, wherein the part of the hot pad covering a knee comprises two strap-shaped parts extended on both sides thereof having means for fastening or attachment.

5. The hot pad assembly of claim 4, wherein the part of the hot pad covering a knee has two strap-shaped parts extended on both sides thereof having fabric hook-and-loop fasteners.

6. The hot pad assembly of claim 1, wherein the first layer and the second layer of the pad cover are similarly shaped.

7. The hot pad assembly of claim 6, wherein the layers comprise a pocket for the hot pad.

8. The hot pad assembly of claim 1, wherein the first layer and the second layer of the pad cover are made of fabric.

9. The hot pad assembly of claim 1, wherein the pad cover comprises means for fastening or attachment on both sides for securing the hot pad assembly around the leg.

10. The hot pad assembly of claim 1, wherein the pad cover comprises fabric hook-and-loop fasteners on both sides for securing the hot pad assembly around the leg.

11. The hot pad assembly of claim 1, wherein the leg cover and pad cover are similarly shaped.

12. The hot pad assembly of claim 1, wherein the leg cover is made of fabric or towel.

13. The hot pad assembly of claim 1, wherein the leg cover is made of plastic wrap.

14. The hot pad assembly of claim 1, wherein the leg cover is disposable.

15. The hot pad assembly of claim 1, wherein the pad cover and the leg cover are integrated into one inseparable unit.

16. The hot pad assembly of claim 1, wherein a beauty product is applied to the leg and the leg cover encloses the product and the leg together.

17. The hot pad assembly of claim 1, wherein the material and thickness of the pad cover and the leg cover are configured to have the temperature of inside leg cover contacting a leg to be 42-46° C. (Celsius).

18. A method for using a hot pad assembly secured to a person's leg for pedicure, comprising steps of:
   applying a beauty product to a leg;
   wrapping or covering the leg with a leg cover such as plastic wrap, towel or fabric;
   placing a pad cover having a hot pad therein on the leg cover for conveying heat from the hot pad to the leg and beauty product(s); wherein the hot pad is yellow soil pad or hwangto pad; and
   securing the pad cover having the hot pad therein around the leg.

19. A method for using a hot pad assembly of claim 18, wherein two strap-shaped parts extended from the part of the hot pad covering a knee are fastened or attached around the knee for securing the hot pad around the knee.

* * * * *